(12) United States Patent
Menon et al.

(10) Patent No.: US 7,354,772 B2
(45) Date of Patent: Apr. 8, 2008

(54) TAG FREE BIO SENSING MICRO STRIP

(75) Inventors: Naresh Menon, 2925 E. Orange Grove Blvd., Pasadena, CA (US) 91107; John D. Minelly, Bothell, WA (US)

(73) Assignee: Naresh Menon, Pasadena, CA (US)

( * ) Notice: Subject to any disclaimer, the term of this patent is extended or adjusted under 35 U.S.C. 154(b) by 43 days.

(21) Appl. No.: 11/120,030

(22) Filed: May 2, 2005

(65) Prior Publication Data
US 2005/0244982 A1     Nov. 3, 2005

Related U.S. Application Data

(60) Provisional application No. 60/568,795, filed on May 7, 2004, provisional application No. 60/567,195, filed on May 3, 2004.

(51) Int. Cl.
| | |
|---|---|
| C12Q 1/68 | (2006.01) |
| G01N 21/00 | (2006.01) |
| H01L 31/00 | (2006.01) |
| G01B 9/02 | (2006.01) |
| H01S 3/00 | (2006.01) |
| H01S 3/08 | (2006.01) |

(52) U.S. Cl. .................... 436/164; 250/214.1; 356/519; 359/337.2; 372/99; 435/6

(58) Field of Classification Search ................ 436/164; 435/6; 250/214.1; 356/519; 359/337.2; 372/99

See application file for complete search history.

(56) References Cited

U.S. PATENT DOCUMENTS 5,216,237 A  *  6/1993  Ritchie et al. ........... 250/214.1
(Continued)

FOREIGN PATENT DOCUMENTS
RU         1819081 A1  *  5/1995
(Continued)

*Primary Examiner*—Jill Warden
*Assistant Examiner*—Lore Ramillano
(74) *Attorney, Agent, or Firm*—Knobbe Martens Olson & Bear LLP

(57) ABSTRACT

A system and method for determining information about an assay. In one embodiment the method includes positioning a filter assembly, having an assay disposed on its surface, relative to a light source such that light from the light source is incident on the filter assembly and at least a portion of the light incident on the filter assembly is reflected from the filter assembly, illuminating the filter assembly with light from the light source, receiving light reflected from the filter assembly in an optical element, analyzing one or more characteristics of the light received in the optical element to determine information about a reaction in the assay, wherein a reaction in the assay results in a change of one or more characteristics of the light received from the filter assembly. In another embodiment, a system for analyzing an assay, comprises a structure in a resonating cavity configured to receive a filter assembly having an assay disposed on a first surface thereof such that the assay is positioned outside the resonating cavity, a light source positioned in the resonating cavity to communicate light to a second surface area of the filter assembly disposed in the resonating cavity, and an analysis system configured to receive light emitted from the filter assembly and detect information about a reaction in the assay based on one or more characteristics of the light.

29 Claims, 5 Drawing Sheets

U.S. PATENT DOCUMENTS

| | | | |
|---|---|---|---|
| 5,229,833 A * | 7/1993 | Stewart | 356/364 |
| 5,502,563 A * | 3/1996 | Dunn et al. | 356/506 |
| 5,513,205 A * | 4/1996 | Rubinstein | 372/99 |
| 5,538,850 A * | 7/1996 | King et al. | 435/6 |
| 5,608,519 A | 3/1997 | Gourley et al. | |
| 5,793,485 A | 8/1998 | Gourley | |
| 5,905,571 A | 5/1999 | Butler et al. | |
| 6,115,401 A * | 9/2000 | Scobey et al. | 372/100 |
| 6,264,328 B1 | 7/2001 | Williams et al. | |
| 6,287,871 B1 | 9/2001 | Herron et al. | |
| 6,771,993 B2 | 8/2004 | Rule et al. | |
| 7,057,720 B2 * | 6/2006 | Caracci et al. | 356/300 |
| 2003/0081309 A1 * | 5/2003 | Nishi et al. | 359/337.2 |
| 2004/0223881 A1 * | 11/2004 | Cunningham et al. | 422/82.05 |
| 2004/0235062 A1 | 11/2004 | Nakajima et al. | |
| 2005/0094158 A1 * | 5/2005 | Paldus et al. | 356/519 |

FOREIGN PATENT DOCUMENTS

| | | | |
|---|---|---|---|
| WO | WO 2004102170 A1 | 11/2004 | |

* cited by examiner

TAG FREE BIO SENSING MICRO STRIP

RELATED APPLICATIONS

This application claims the benefit of U.S. Provisional Application No. 60/568,795 filed May 7, 2004, titled "TAG FREE BIO SENSING MICRO STRIP" and U.S. Provisional Application No. 60/567,195 filed May 3, 2004, titled "FIBER LASER FREQUENCY TUNING MECHANISM," both of which are incorporated by reference in their entireties.

BACKGROUND OF THE INVENTION

1. Field

The field of the invention relates to laser analyte detection systems and methods.

2. Description of the Related Technology

Microarray assays can be used to determine the presence of an analyte or compare genetic expression between two or more sample groups on thousands of genes per experiment. Typically, labels (e.g., secondary identifier tag) are used to detect the bio-molecular interactions, usually employing luminescent detection principles such as fluorescence, bioluminescence, or chemiluminescence, to detect the presence of specific chemical species. The array results are useful in molecular disease classification, gene and pathway discovery, tumor prognosis and sub-classification, drug development, and the prediction of response to treatment. However, such experiments have suffered from multiple problems including artifacts in sample preparation and labeling, software definition of each spot or feature, determination of signal level, and reproducibility of signals within a single array or across arrays. For example, experimental variations within a tissue source or type are often larger than the distinguishing differences, e.g., between cancerous and non-cancerous expressions.

Typically, laser-based systems used for analyte detection also require labels to detect bio-molecular interactions and require direct exposure of the sample to a laser beam, which can complicate the detection process. Accordingly, there is a need to develop an alternative method for gene expression measurements that overcomes the above-described and other problems in the art.

SUMMARY OF CERTAIN INVENTIVE ASPECTS

The system, method, and devices of the invention each have several aspects, no single one of which is solely responsible for its desirable attributes. Without limiting the scope of this invention as expressed by the claims which follow, its more prominent features will now be discussed briefly. After considering this discussion, and particularly after reading the section entitled "Detailed Description of Certain Embodiments," one will understand how the features of this invention provide advantages that include, in a first embodiment, a method of determining information about an assay, including positioning a filter assembly, having an assay disposed on its surface, relative to a light source such that light from the light source is incident on the filter assembly and at least a portion of the light incident on the filter assembly is reflected from the filter assembly, illuminating the filter assembly with light from the light source, receiving light reflected from the filter assembly in an optical element, analyzing one or more characteristics of the light received in the optical element to determine information about a reaction in the assay, where a reaction in the assay results in a change of one or more characteristics of the light received from the filter assembly.

In one aspect of the first embodiment, the light source comprises a laser light source. In another aspect of the first embodiment the characteristic of the light that is analyzed is wavelength. In another aspect, the method further includes disposing the assay on the filter assembly, and exposing the assay to one or more reagents. In another aspect, the assay is disposed on a first surface of the filter assembly and the light from the light source is incident on a second surface of the filter assembly. In some embodiments, the method further comprises collimating the light from the light source before it is incident on the filter assembly, and collimating the light reflected from the lens assembly before it is received in the optical element. In another aspect of the first embodiment, the reaction in the assay results in a physical change in the assay that changes the refractive index of the surface of the filter assembly on which the assay is disposed. In yet another aspect, analyzing the received light comprises analyzing one or more characteristics of the light received from the filter assembly after a physical change has occurred in the assay in relation to one or more characteristics of the light illuminating the filter assembly before the physical change occurred in the assay. The light source can include a broadband light source and a filter configured to transmit one or more wavelengths. In another aspect, the method further includes positioning the filter assembly further comprises positioning the filter assembly such that the assay is disposed on the opposite side of the filter assembly as the incident light.

A second embodiment includes a method of determining information about an assay disposed on a first surface of a filter assembly, including incorporating the filter assembly in an optical resonating cavity such that the assay is disposed exterior to the resonating cavity, providing light to the filter assembly such that at least a portion of the light incident on the filter assembly is reflected by the filter assembly into the optical resonating cavity, receiving at least a portion of the light from the optical resonating cavity, and determining information about a reaction in the assay by analyzing one or more characteristics of the received light where a reaction that occurred in the assay results in a physical change in the assay that is manifested in one or more characteristics of the light in the optical cavity. In one aspect of the second embodiment, the filter assembly is configured to change the wavelength, intensity, and/or phase of light in the resonating cavity when a reaction occurs in the assay. In a second aspect, the characteristic of the light that is analyzed is its wavelength. In some configurations, the light source comprises a broadband light source and a filter configured to transmit one or more wavelengths. In other configurations, the light source comprises a laser light source.

A third embodiment includes a system for analyzing an assay, including a structure having a resonating cavity configured to receive a filter assembly having an assay disposed on an assay receiving portion of the filter assembly, such that the assay receiving portion is positioned exterior to said resonating cavity, a light source positioned to provide light to the filter assembly when the filter assembly is received by said structure such that light from the light source impinges on the filter assembly and at least a portion of the light is reflected from the filter assembly into the resonating cavity, an optical element for receiving light reflected from the filter assembly, and an analysis system connected with said optical element and configured to detect one or more characteristics of the light received by said optical element and determine information about a reaction of the assay based on the one or more detected characteristics. In one aspect, the optical element is positioned within the resonating cavity. In another aspect of the third embodiment, the system further includes the filter assembly. In another aspect, the system further includes a lens assembly for collimating light, said lens assembly positioned in said resonating cavity relative to said laser light source and said optical element such that light from the laser light source propagates through said lens assembly and light reflected from the filter assembly propagates through said lens assembly. In another aspect, the filter assembly comprises a Fabrey-Perot etalon filter.

A fourth embodiment includes a system for analyzing an assay, including a structure including a resonating cavity configured to receive a filter assembly such that an assay disposed on a surface of the filter assembly is positioned outside said resonating cavity, and an analysis system configured to receive light emitted from the resonating cavity and further configured to detect information about a reaction in the assay based on the light received from the resonating cavity where a reaction in the assay results in a change to one or more characteristics of the light in the resonating cavity. In an aspect of the fourth embodiment, the system further includes the filter assembly.

A fifth embodiment includes a filter assembly configured to form a portion of a laser resonating cavity of a system that determines information about an assay by analyzing light emitted from the laser resonating cavity, the filter assembly including an optical structure comprising one or more filters configured to receive light from a light source through a first surface and reflect at least a portion of the received light, and an assay disposed on a second surface of said optical structure, said second surface being disposed substantially parallel to and opposite said first surface where said assay is configured to optically interact with said optical structure to change an optical characteristic of the light propagating through the laser resonating cavity based on a reaction that occurs in the assay. In one aspect, the optical characteristic changed by a reaction in the assay is the wavelength. In another aspect, the assay and optical structure interact to change one or more properties of the laser resonating cavity that affects the wavelength of light emitted from the resonating cavity.

A sixth embodiment includes a system for determining information about an assay, including means for positioning a filter assembly, having an assay disposed on its surface, in a resonating cavity relative to a light source such that light from the light source is incident on the filter assembly and at least a portion of the light incident on the filter assembly is reflected from the filter assembly, means for illuminating the filter assembly with light from the light source, means for receiving light reflected from the filter assembly in an optical element, means for analyzing one or more characteristics of the light received in the optical element to determine information about a reaction in the assay, wherein a reaction in the assay results in a change of one or more characteristics of the light received from the filter assembly.

DETAILED DESCRIPTION OF CERTAIN EMBODIMENTS

The following detailed description is directed to certain specific embodiments of the invention. However, the invention can be embodied in a multitude of different ways as defined and covered by the claims. In this description, reference is made to the drawings wherein like parts are designated with like numerals throughout.

Embodiments of the invention include methods and systems for determining the presence, concentration, or amount of a substance in a fluid. Such methods and apparatus have applicability in the field of clinical analysis, but also, for example, in wet chemical analysis in general, and in gas analysis. The embodiments relate to methods and systems/devices that, as a consequence of a biochemical interaction, will alter one or more characteristics of light from a laser (e.g., optical fiber lasers). The embodiments can include a laser that changes its lasing frequency as a function of changes in its cavity parameters. The laser used for some embodiments can produce a laser beam over a large bandwidth. For example, some embodiments include a fiber laser that provides gain over a wavelength span of about 30 nanometers (nm) when the laser cavity of the fiber laser changes due to the presence of an analyte disposed such that it influences the parameters of the laser cavity. In some embodiments, the presence of an analyte in an appropriately prepared assay can be detected by analyzing the change in one or more characteristics of a laser beam, e.g., wavelength, phase, intensity, or frequency.

Figure 1:
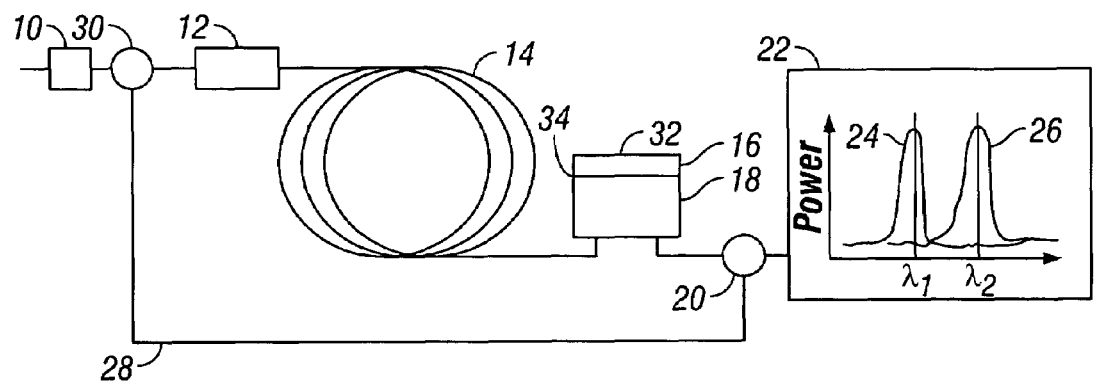
FIG. 1 is a schematic diagram illustrating one embodiment of a bio-sensor system having a sensor site for detecting an analyte without the aid of secondary identifier tags.

FIG. 1 illustrates one embodiment of the invention, comprising a system having a single sensor site for detecting an analyte without the aid of secondary identifier tags. The system includes an optical pump 10 coupled to a gain medium 14 via an optical coupler 30 and an optical isolator 12. The gain medium 14 can be an appropriately doped optical fiber, as shown in this embodiment, where the doping can be, for example, erbium, thulium or a combination thereof.

The first optical coupler 30 is disposed between the optical isolator 12 and the optical pump 10 and configured such that light from the optical pump 10 passes through the first optical coupler 30 to the optical isolator 12. The first optical coupler 30 is also coupled to one end of an optical fiber 28. The optical isolator 12 is disposed between the first optical coupler 30 and the gain medium 14 to regulate the direction of the propagation of light from the optical pump 10, through the first optical coupler 30, through the optical isolator 12 to the gain medium 14.

The gain medium 14 is connected to a sensor site 34 which includes an optical assembly 18 configured to receive and couple to a filter assembly 16. The filter assembly 16 has a biochemical assay 44 (FIG. 5) disposed on a portion of its surface 32. The combination of the filter assembly 16 and the biochemical assay 44 are referred to herein as the "sensor 34." When the filter assembly 16 is coupled to the optical assembly 18, it becomes part of a laser resonating cavity and the surface 32 having the assay is disposed exterior to the resonating cavity. When the filter assembly 16 is coupled to the optical assembly 18, the optical assembly 18 is configured to receive light from the gain medium 14, and propagate the light so that it is incident on a surface of the filter assembly 16 disposed within the resonating cavity. The presence of an analyte as detected by the assay 44 on the surface 32 changes the refractive index of the filter assembly 16, which changes one or more characteristics of the light in the resonating cavity.

In some embodiments, the filter assembly 16 can include a reflective filter, e.g., a Fabrey-Perot etalon filter. The reflective filter can have one or more layers, where each layer can have the same or different optical properties. In some embodiments, the filter assembly 16 can include a Bragg reflector. In some embodiments, the filter assembly 16 can include a Fabrey-Perot resonating cavity filter. In some embodiments, the filter assembly 16 can include a transmission filter, e.g., a fiber Fabrey-Perot etalon filter, a fiber-coupled Fabrey-Perot micro-etalon filter, or the like. The transmission filter can have one or more layers, where each layer can have the same or different optical properties. In some embodiments, the filter assembly 16 can include a reflection filter, e.g., a fiber Bragg grating filter, a set of sampled fiber Bragg gratings, a Fabrey-Perot etalon filter, or the like. By providing the filter assembly 16 with particular optical characteristics, the frequency of the fiber laser can be latched, e.g., the lasing frequency can be set or "locked" to a particular frequency value. In some embodiments, the filter assembly 16 can be a fiber coupled assembly, which can include dissimilar fiber waveguides.

A second optical coupler 20 connects the optical assembly 18 to the optical fiber 28 and also to an analyzer 22. In some embodiments, the analyzer 22 includes a spectrum analyzer. The second optical coupler 20 directs a portion of the light it receives from the optical assembly 18 to the optical fiber 28 and a portion to the analyzer 22. For example, in one embodiment the second optical coupler 20 directs about 5% of the light it receives to the analyzer 22 and about 95% to the optical fiber 28. Accordingly, a circulating loop is formed that propagates light through the optical isolator 12, the gain medium 14, the optical assembly 18, and the optical fiber 28. In this embodiment, this loop constitutes the resonating cavity. Perturbing the loss profile of the resonating cavity results in a shift in optical wavelength and power of the laser. The loss profile can be changed by replacing the optical filter assembly 16 having certain optical properties with another optical filter assembly 16 having one or more different optical properties. It will be appreciated that in some embodiments, the resonating cavity can include planar waveguide elements instead of one or more of the parts described herein. In some embodiments, a linear laser cavity is used.

The laser light in the resonating cavity will have known optical characteristics based on the optical properties of the filter assembly 16. It will be appreciated that if the optical properties of the filter assembly 16 change, the optical characteristics of the laser light can also change. The optical characteristics of the filter assembly 16 can be so designed and configured such that one or more optical characteristics of the filter assembly 16 are influenced by changes that occur to one or more of its surfaces. For example, a change occurring in a biochemical reaction site (e.g., an assay) disposed on the surface 32 of the filter assembly 16 can result in a change in the refractive index at surface 32. Changing the refractive index at a single surface, e.g., the surface 32 disposed on the outside of the optical assembly 18 in this embodiment, can affect one or more other optical characteristics of the filter assembly 16. For example, a change in the refractive index at any filter surface including any intermediate layer of the filter assembly 16 can result in a change in the wavelength dependant loss of the filter assembly 16. By detecting whether a change in the wavelength has occurred, information about a reaction in the assay can be determined.

It will be appreciated that the analyzer 22 can be configured to determine optical characteristics of the light it receives from the optical assembly 18. In some embodiments, the analyzer 22 can read the optical wavelength, and/or the shift in wavelength that results from a change in optical characteristics of the filter assembly 16. In one embodiment, the analyzer 22 can determine the shift in lasing frequency of the fiber laser by scanning for the filter position that corresponds to the maximum optical power and correlating the filter position to a wavelength value.

Still referring to FIG. 1, Graphs 24 and 26 shown in the analyzer 22 are examples of representations of the wavelength of the laser light in the resonating cavity (x-axis) verses optical power (y-axis) for the system In a first state, represented by graph 24, the system is configured with a filter assembly 16 having a first assay disposed on one of its surfaces 32 that is exterior to the optical assembly 18. The first assay is not bound to an analyte and therefore graph 24 represents a first state of the system with a first set of optical characteristics associated with the laser light. In this example, the analyzer 22 has determined the optical power of graph 24 is greatest at $\lambda_1$. In the second state, represented by graph 26, the system is configured such that the filter assembly 16 has a second assay disposed on one of its surfaces 32 that is exterior to the optical assembly 18. The second assay is bound to a target analyte and therefore graph 26 represents a second state of the system with a second set of optical characteristics associated with the laser light. In this example, the analyzer 22 has determined that the optical power illustrated in graph 26 is greatest at $\lambda_2$. In this example, the shift in wavelength from $\lambda_1$ to $\lambda_2$ indicates the presence of the analyte in the second assay.

The laser output optical wavelength and power are extremely sensitive to the various elements of the laser system. The double pass gain of a laser may be approximated with the following mathematical expression:

$$\text{gain}(\lambda) \approx G(\lambda)^2 R_1(\lambda) R_2(\lambda) e^{(-2\alpha(\lambda)L)} \qquad \text{Equation 1}$$

In Equation 1, $\lambda$ is the optical wavelength of the laser output, G is the single pass gain of the optical gain medium, $R_1$ and $R_2$ are reflectance values of the cavity mirrors, alpha is the passive loss and L is the cavity length. Typically, a broadband laser emits power at a wavelength that corresponds to the wavelength at which the laser resonating cavity has the lowest loss. It will be appreciated that an appropriate broadband filter can be designed such that the minimum wavelength dependent loss occurs at the desired lasing frequency. It will also be appreciated that the reflectance properties of the lasing cavity can be used to preferentially select the lasing wavelength. A shift in the wavelength of the reflector alters the resonating cavity by providing maximum gain at a different wavelength. As seen by Equation 1, the correlation between the gain at a certain wavelength and the wavelength of the reflector is linear.

It will be appreciated that in some embodiments, a broadband light source and a filter configured to select predetermined wavelengths can be used instead of a laser light source.

Figure 2:
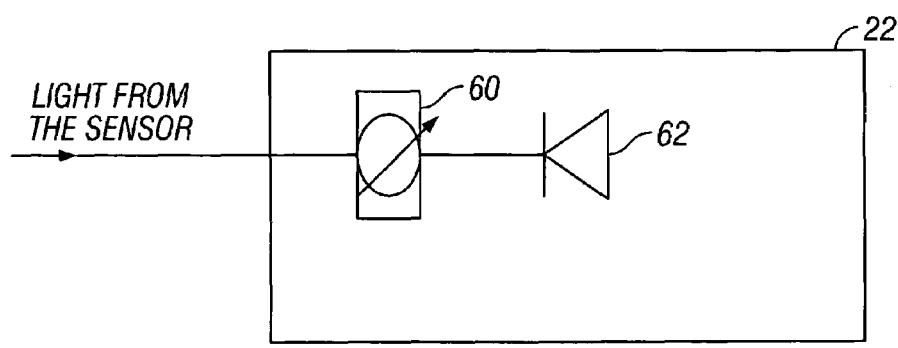
FIG. 2 is a schematic illustrating one embodiment of an analyzer having a tunable filter and a photodiode.

FIG. 2 is a schematic diagram illustrating an alternative embodiment of the analyzer 22, where the analyzer 22 can determine the wavelength of the light exiting optical assembly 18 using an optical filter and sensor. There are a variety of commercially available analyzers 22 that can be employed to determine a shift in wavelength of the light exiting the sensor 16 (FIG. 1). A suitable analyzer 22 to determine a change in wavelength can also be formed using less expensive means. In one embodiment, the analyzer 22 includes a tunable filter 60, positioned to receive light from the optical assembly 18, and a photo diode 62 positioned to receive light from the tunable filter 60. As shown in FIG. 2, to determine if a change has occurred in an assay on the filter assembly 16 (FIG. 1), light propagating from the sensor 34 (FIG. 1) is communicated into the analyzer 22 and enters the tunable filter 60. The pass band of the tunable filter 60 can be controlled, automatically or manually, to scan the optical bandwidth of interest for the light, for example, an optical bandwidth that includes wavelengths $\lambda_1$ and $\lambda_2$ as shown in FIG. 1. The photodiode 62 receives light passing through the tunable filter 60 during the time period that the tunable filter 60 is scanning the optical bandwidth of interest. The output current of the photodiode 62 correlates to the total amount of light that exits the tunable filter 60 at each scanned wavelength. By scanning the entire optical bandwidth of interest with the tunable filter 60 while the tunable filter 60 is receiving light from the optical assembly 18, the maximum measured current output by the photodiode 62 can be identified and correlated to the maximum power and wavelength of the signal exiting the optical assembly 18. Accordingly, a shift in wavelength, for example, from $\lambda_1$ to $\lambda_2$ (FIG. 1) can be identified, which indicates the presence of the analyte in an assay disposed on the filter assembly 16 (FIG. 1).

Figure 3:
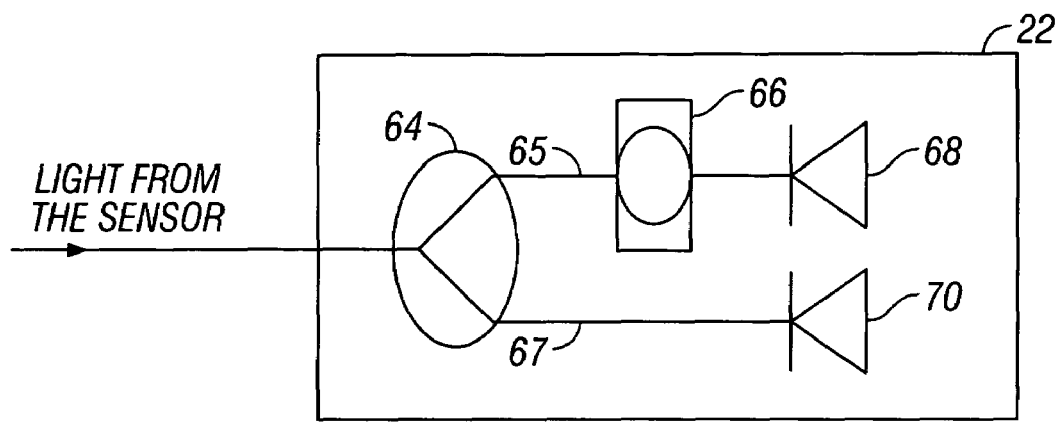
FIG. 3 is a schematic illustrating one embodiment of an analyzer having a filter and two photodiodes.
Figure 4:
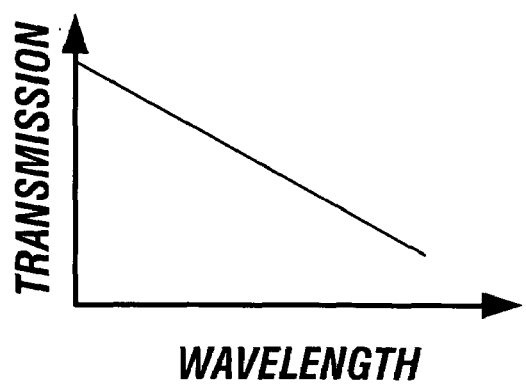
FIG. 4 is a graph illustrating an example of a filter response of the filter shown in FIG. 3.

FIG. 3 illustrates another embodiment of the analyzer 22. As shown in FIG. 3, the analyzer 22 in this embodiment includes an optical splitter 64 positioned to receive light propagating from the sensor 34 (FIG. 1). The analyzer 22 also includes a static filter 66 positioned to receive light from the optical splitter 64, and a first photodiode 68 positioned to receive light from the static filter 66 and a second photodiode 70 positioned to receive light from the optical splitter 64. The static filter 66 has a known spectral response, which can be the filter spectral response shown in FIG. 4. The analyzer 22 is configured so that light from the sensor 34 enters the analyzer 22 and is split by the optical splitter 64 so that it propagates along a first path 65 and a second path 67. Light propagating along the first path 65 passes through the static filter 66 and is received by the first photodiode 68. Light propagating along the second path 67 is received by the second photodiode 70. The output current of the first photodiode 68 and the second photodiode 70 correlate with the signal that each photodiode receives. By comparing the output of the two photodiodes 68, 70 and knowing the spectral response of the static filter 66, one can compute the total power and wavelength of the signal leaving the sensor 34 at any time using the following equations:

$$P = 2Pd_2 \quad \text{Equation 2}$$

$$\lambda = g(Pd_1/Pd_2) \quad \text{Equation 3}$$

where P is the power of the signal, $\lambda$ is the wavelength of the signal, $Pd_1$ is the voltage at the first photodiode 68, $Pd_2$ is the voltage at the second photodiode 70, and g( ) is the known response function of the static filter 66. In another embodiment (not shown), the sensor 34 (FIG. 1) has a certain spectral response so that a change in the assay results in a known change in power in the light from the sensor. In such an embodiment, a single photodiode can be configured in the analyzer 22 to receive and monitor the light from the sensor 34 to identify a relevant power change, and the analyzer 22 can determine a change in the assay based on detecting the known change in power.

The embodiment shown in FIG. 1 can also be incorporated into a high throughput system ("HTS") for analyzing numerous assay reaction spots disposed on a filter assembly 16. For example, the filter assembly 16 can be formed by a strip that has up to 50 or more reaction spots disposed on its surface. Numerous strips can be joined together to form a microarray comprising rows and columns of reaction spots. In some embodiments, the high-throughput system can have up to 40,000 spots formed into a microarray on the filter assembly 16. In some embodiments, a high-speed X-Y scanning process can be employed to determine information about the reaction in each of the spots in the microarray, where the filter assembly 16 is stepped in one direction (e.g., X) and the scanning is done in the other direction (e.g., Y).

Figure 5:
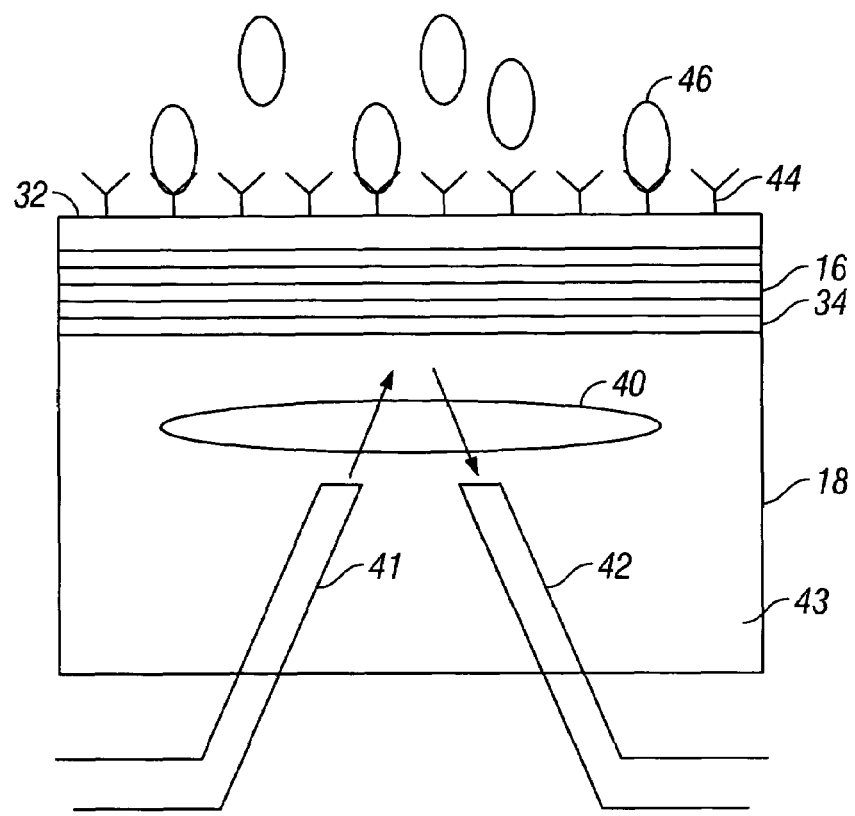
FIG. 5 is a schematic diagram of an optical assembly for use in a bio-sensor system, the assembly configured with a filter assembly having a reflective thin-film stack.
Figure 6:
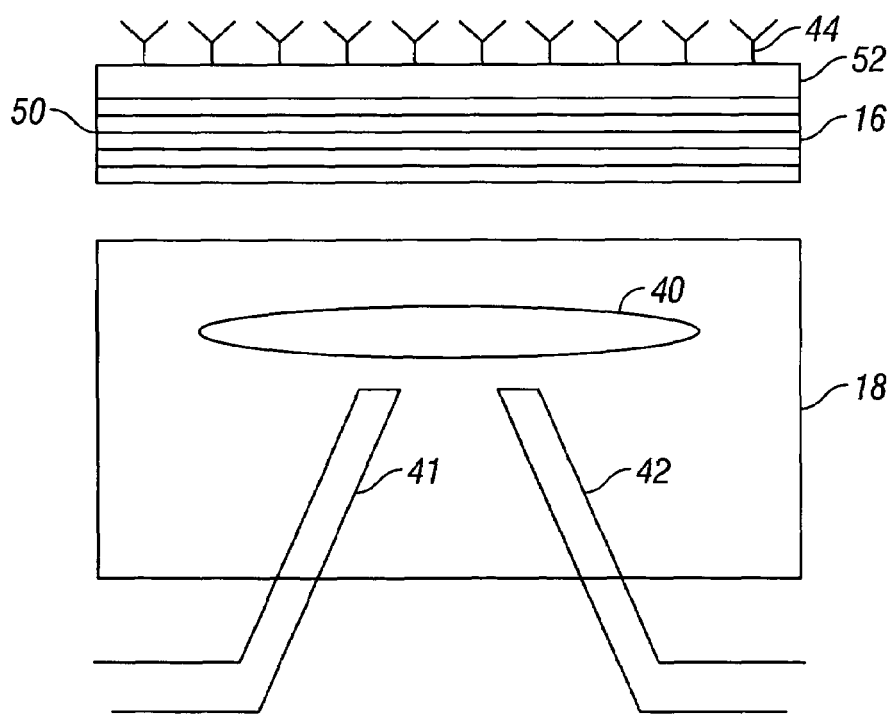
FIG. 6 is a schematic diagram of the optical assembly and filter assembly shown in FIG. 5 with the filter assembly removed from the optical assembly.

FIG. 5 illustrates a more detailed view of the embodiment of the optical assembly 18 and filter assembly 16 of FIG. 1. Here, the optical assembly 18 is illustrated with the filter assembly 16 secured thereto. As shown in FIG. 6, the filter assembly is removable from the optical assembly. In some embodiments, the filter assembly 16 or parts of the filter assembly 16 can be made to be disposable. In this embodiment, the filter assembly 16 is configured as a reflection filter. Light from the gain medium 14 (FIG. 1) enters the optical assembly 18 through an entrance fiber ferrule 41. A lens assembly 40 comprising one or more optical elements is positioned between the entrance fiber ferrule 41 and the filter assembly 16 so that it collimates light emitted from the entrance fiber ferrule 41 and provides the collimated light to the filter assembly 16. In some embodiments, the lens assembly 40 comprises one or more lenses to collimate the light. The lens assembly 40 also collimates the light reflected by the filter assembly 16 such that the reflected light propagates into exit fiber ferrule 42. A portion of the light that enters the exit fiber ferrule 42 is provided to the analyzer 22 (FIG. 1) and a portion is provided to the optical fiber 28 (FIG. 1) which is configured to circulate the light through the gain medium 14 (FIG. 1).

A biochemical reaction site can be formed by depositing an assay 44 on the surface 32 of the filter assembly 16. The assay 44 is disposed outside the cavity in the optical assembly 18, e.g., on an exterior surface of the filter assembly 16 when the filter assembly 16 is secured to the optical assembly 18. While one surface 32 is exposed to a bio-molecular reaction, the opposite surface is coupled optically to the fiber laser ensemble, forming a part of the lasing cavity.

It will be appreciated that the assay 44 is configured such that the reaction of the assay 44 with a target analyte 46 results in a physical change of the assay that results in a change of one or more optical properties of the filter assembly 16. Depending on the particular configuration of an embodiment, reagents and samples can be exposed to the assay 44 in numerous ways. For example, one of the numerous microfluidic flow systems can be used to control the exposure of the assay 44 to reagents and samples. Microfluidic flow systems are available commercially and can be adapted for this application. Also, micropipettes can be used to provide samples and reagents to the assay 44. In some embodiments, the micropipettes are used manually, in other embodiments the micropipettes are incorporated in a system to apply the samples and reagents to the assay 44 automatically. In a further embodiment, the assay 44 can be exposed to the samples and reagents by dip-coating, for example, dipping the assay 44 in the desired sample or reagent.

Changes to the assay 44, e.g., a change of thickness of the bio-molecular layer of the assay, a change in the refractive index, or both, can result in a change (e.g., a distortion) of the signal reflected by the filter assembly 16 inside the optical assembly 18. For example, when the assay 44 is exposed to a target analyte 46, the assay 44 binds to the target analyte 46 and the assay 44 becomes thicker and/or the assay 44 changes the refractive index at the surface 32 that it is disposed upon. The effect of this change is significantly amplified within the lasing cavity and results in a change in one or more characteristics of the laser light. For example, this change can result in a shift in the resonating wavelength of the laser. Knowing the characteristics of the laser light produced in the resonating cavity before the biochemical reaction takes place in the assay 44, a detected change in a characteristic of the laser light can be correlated to a biomolecular event in the assay 44.

The optical assembly 18 can be configured to receive and hold the filter assembly 16 so that a biochemical reaction in the assay 44 can be detected and analyzed. In some embodiments, the filter assembly 16 can be optically coupled to the entrance fiber ferrule 41 and the exit fiber ferrule 42. In some embodiments, the filter assembly 16 can be incorporated in a structure that is optically coupled to the optical assembly 18. The filter assembly 16 can be coupled to the optical assembly 18 in a variety of ways to ensure the filter assembly 16 is positioned in the path of the optical beam emitted from the entrance fiber ferrule 41. For example, in one embodiment, a tongue and groove configuration can be used where the filter assembly 16 is mechanically aligned to the optical assembly 18. In another embodiment, a pin assembly can couple the filter assembly 16 to the optical assembly 18. In some embodiments, the filter assembly 16 is first automatically aligned with the optical assembly 18 using fiducials on the filter assembly 16 that are read by a system (not shown) that provides feedback as to the alignment of the filter assembly 16. In one such embodiment, the feedback system includes using an optical feedback system. In some embodiments, the feedback system includes using an electrical or electronic feedback system. In some embodiments, the feedback system includes a combination of electrical and optical systems. Once the filter assembly 16 is aligned with the optical assembly 18, the filter assembly 16 can be coupled to the optical assembly 18 using various mechanical coupling means, including, for example, a micro gripper, or air suction (e.g., a vacuum).

FIG. 6 illustrates an embodiment where the filter assembly 16 can be removed from the optical assembly 18 so that another filter assembly 16 can be received in its place. The optical assembly 18 can receive a variety of filter assemblies which each can be configured with a particular filter, e.g., one of the filters described above.

In one embodiment, the filter assembly 16 includes a thin-film reflectance filter 50 having one or more layers and a overlay or sensing layer 52. In one embodiment, the thin film filter 50 includes 10 alternating layers of SiO and $SiO_2$. The filter assembly 16 has reflection characteristics of a raised cosine 100 nm or less in bandwidth and 100% deep such that a change in the refractive index of the overlay region 52 results in a linear shift in the center wavelength of the filter. In one embodiment, the filter assembly 16 is configured to have the greatest possible shift in center wavelength (CW) when the overlay layer 52 has a thickness of about 1 nm and a refractive index of about 1.38. The characteristics of one embodiment of the filter assembly 16 are shown in Table 1 (below).

TABLE 1

| Parameter | Value | Comment |
| --- | --- | --- |
| Filter Bandwidth (BW) | <100 nm | Operates in the L band. |
| Start Wavelength | 1540 nm | |
| Stop Wavelength | 1640 nm | |
| Center Wavelength (CW) | 1580 nm | Defined as the wavelength corresponding to maximum reflectance. |
| Filter Depth (D) | >40 nm | The change in reflectance from CW to CW + BW/2 |
| Sensitivity (S) | >0.1 nm/nm | The change in CW as a function of thickness of overlay layer where the overlay layer has a refractive index (RI) of 1.38 |
| Optical Power | 500 mW | Maximum optical power incident on filter |
| Out of bandwidth performance | None | Optical characteristics outside the bandwidth are not specified. |
| Temperature Dependence | <0.1 pm/° C. | Defined as the shift in center wavelength of the filter as a function temperature. |
| Filter Substrate | None | No constraints on the choice of filter substrate |

Using the terminology defined in Table 1, a figure of merit (FOM) is defined for the filter assembly as:

$$FOM = \frac{D*S}{BW} \qquad \text{Equation 4}$$

where D is the filter depth, defined as the change in reflectance from center wavelength ("CW") to CW+BW/2, BW is the filter bandwidth, and S is the sensitivity. The ideal filter could have a peak reflectivity of unity, minimum reflectivity of zero (D=1), a narrow optical bandwidth and a high sensitivity. In practice, these parameters can be selected based on the constraints of a particular implementation. In one embodiment, the objective of the design is to maximize the FOM. In one embodiment, the filter assembly has a filter bandwidth (BW) of less than about 100 nm, a peak reflectivity of about 40% and a rate of change of around 0.1 nm.

Figure 7:
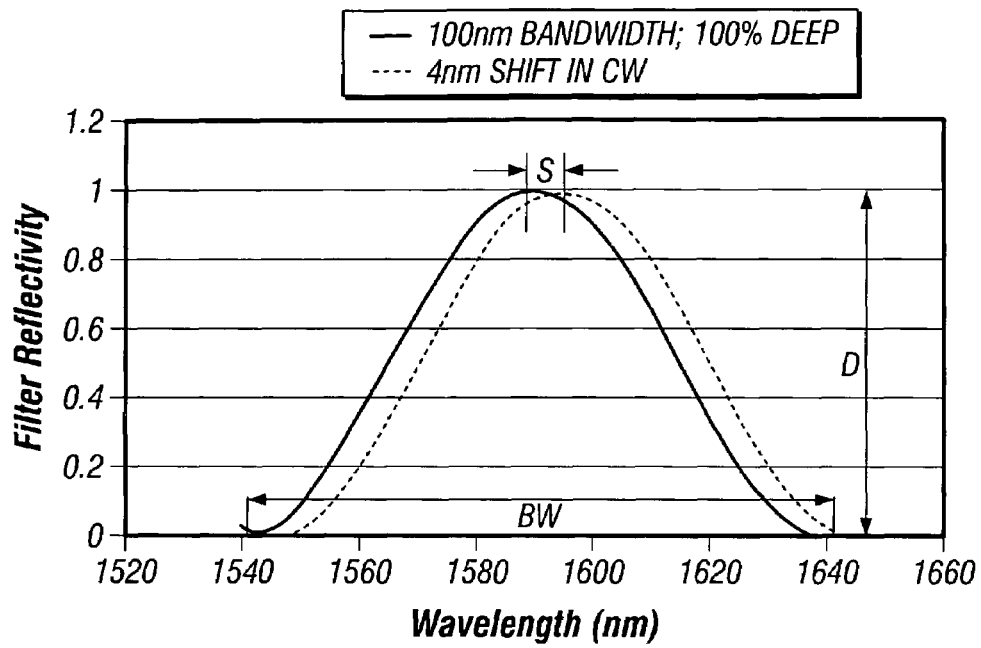
FIG. 7 is a graphical diagram illustrating the definition of filter performance parameters of the filter assembly shown in FIG. 5.

The parameters Center Wavelength (CW), Filter Depth (D), and sensitivity (S) are graphically illustrated as an example of one embodiment in FIG. 7.

Figure 8:
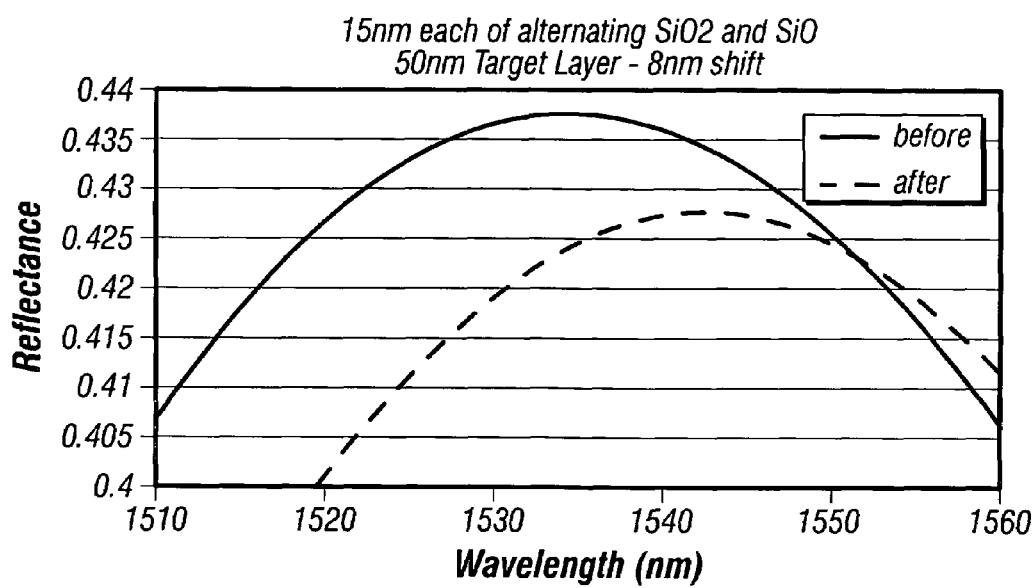
FIG. 8 is a graphical diagram of reflectance as a function of wavelength for one embodiment of the filter assembly shown in FIG. 5.

FIG. 8 illustrates the relationship between wavelength and reflectance of one embodiment of a filter assembly having a sensitivity (S) of 0.1, a filter bandwidth (BW) of 100 nm, and a filter depth of 30% from its peak reflectivity.

Figure 9:
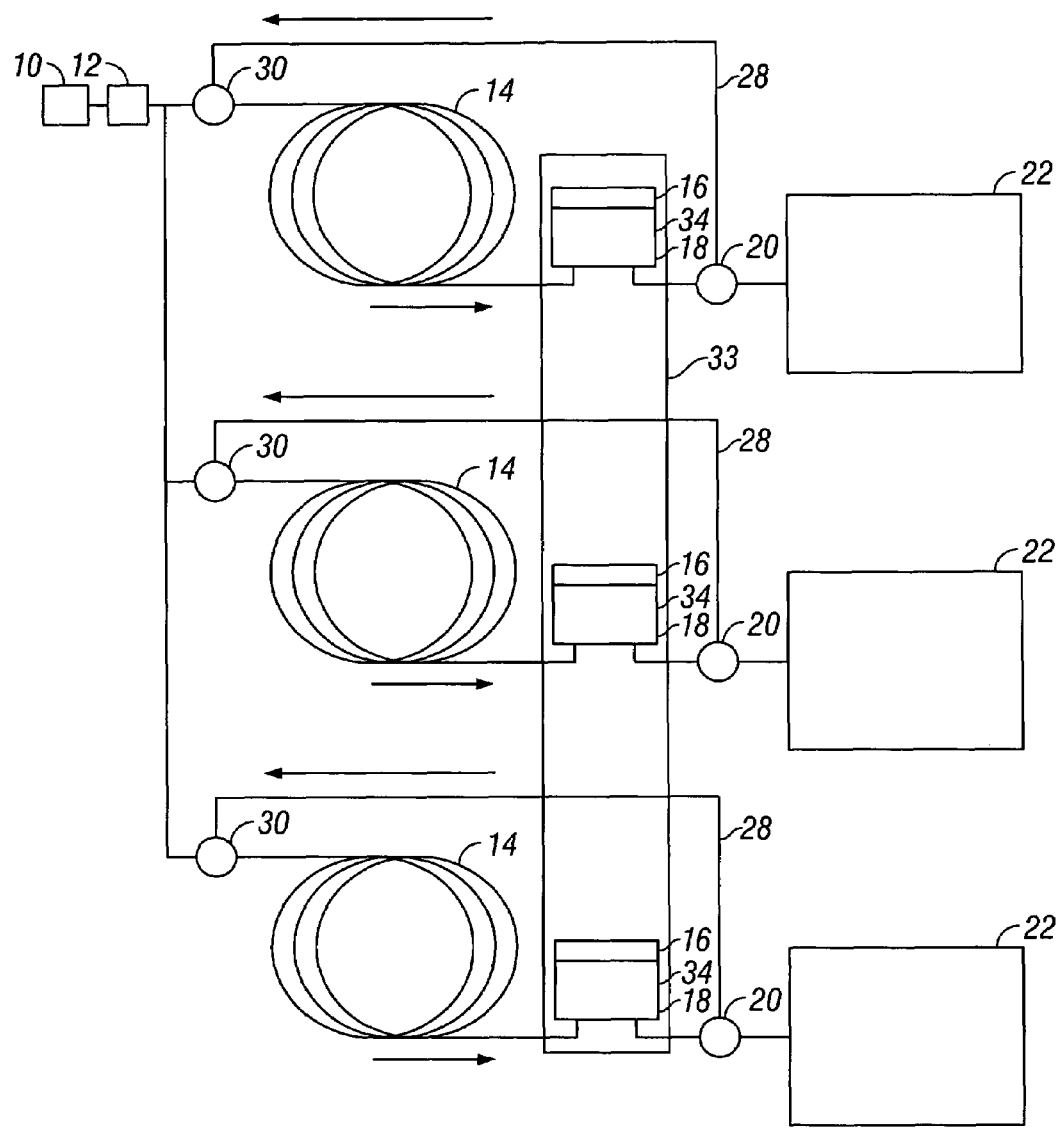
FIG. 9 is a diagram illustrating one embodiment of a bio-sensor system having multiple sensor sites for detecting an analyte without the aid of secondary identifier tags.

FIG. 9 illustrates an embodiment of a system that includes multiple resonating cavities and an array 33 of sensor sites 34 (e.g., biochemical reaction sites), each sensor site 34 including an optical assembly 18 and a filter assembly 16. In some embodiments, the sensor sites 34 can be arranged on a single fixture which can be configured such that the entire fixture is disposable or reusable. Configurations incorporating multiple sensor sites allow the arrangement of multiple biochemical interactions on the sensor sites 34 which can be independently monitored to determine the results of reactions in the assays.

It will be appreciated that many embodiments of the array 33 are considered for testing analytes with multiple sensor sites. For example, in one embodiment, the multiple sensor sites in the array 33 can contain the same assay designed to detect the same analyte. In another embodiment, the multiple sensor sites in the array 33 can contain different assays designed to detect different analytes. In one embodiment, the sites in the array 33 include a set of two or more similar assays where the assays include differences designed to detect one or more particular characteristics of an analyte present in a sample. For example, a set of assays can be designed to detect the concentration of an analyte present in the samples. In some embodiments, a particular characteristic can be detected by analyzing which assay(s) in the set reacted, where in other embodiments the analysis of the reactions that occurred in two or more assays in the set of assays yields information on a particular characteristic of the analyte, or on a unique combination of the analytes present.

Various configurations of the sites in the array 33 can be used depending on the implementation desired. In one embodiment the sites in the array 33 can be used to detect an analyte from a single sample. In another embodiment, the sites in the array 33 can be used to detect an analyte from a plurality of samples. In some embodiments, the sites in the array 33 can be designed so that the results from two or more sites in the array 33 can be used to detect different combinations of analytes in a given sample, which can convey information regarding the source, content, health, and/or quality of the sample. In addition, multiple sensor sites can be used to determine information of multiple analytes in a sample, where the different combination of analytes present in a given sample convey a message regarding the source, content, health or quality of the subject from which the sample was extracted.

Three resonating cavities are shown in the embodiment of FIG. 9, but it will be appreciated that embodiments can include two resonating cavities or more than three resonating cavities. A single optical pump 10 for generating pump radiation can be shared among the resonating cavities, as shown. In some embodiments, multiple optical pumps can be used. FIG. 9 illustrates representations of three analyzers 22 that receive and analyze the light from the sensor sites 34. In practice, a single analyzer can be configured to receive the light from multiple sensor sites 34 (e.g., in a sequence using an optical switch) and analyze one or more characteristics of each. In some embodiments, a single wavelength detecting analyzer 22 is shared by all the resonating cavities using an optical MUX assembly. In some embodiments, the analyzer 22 can determine a characteristic of the light using a photodiode and a tunable narrow band filter, as described above in reference to FIGS. 2-4. In some embodiments, the analyzer 22, or another system that receives data from the analyzer 22, can generate a report describing the results of the analyte testing. The report can include the status of the assay, for example, whether binding has occurred, and/or how much binding has occurred. This report is typically provided to the user. In some embodiments, the report is communicated to a third party, for example a point-of-care service, via a wired or wireless communications means, for example, a modem, facsimile machine, or the internet.

In some embodiments, the analyzer 22 includes a system having a signal processing unit (not shown) that monitors each of the biochemical reaction sites, and interprets and reports on the reactions occurring at one or more sensor sites 34. Signal processing analysis includes using the multiple calibration information, real time information of the environmental conditions and effects on the system and the signal from the sensor to determine the binding status of the assay 44. In some embodiments, the signal processing unit interprets results from multiple biochemical sites and provides the user information of the biochemical reactions (e.g., the kinetics) occurring at each site. One advantage of the embodiments described herein is that process variations during manufacturing of the pieces used in the instrument can be factored into the calibration of the system. The signal processing can include using multiple calibration information, real time information on the environmental effects on the system, and the signal from the sensor 34 to determine information of the binding of the assay.

Depending on the configuration of an embodiment, custom software and electronics can monitor the light from the sensor site 34 or a signal derived from the light (e.g., an electrical signal) and report changes in the assay. The system can address one or more of a number of factors to report on the status of biochemical interactions at the sensor, including, for example, system calibration including variations in quality of the assay, instrument and sensor, environmental components (e.g., temperature and pH), long term changes in the system components of the assay (e.g., laser source and assay lifetime), and the relative positioning of the filter assembly 16 with the optical assembly 18 can be sensed and the sensor signal compensated accordingly. In an embodiment that includes an array of sensors 34, for example as shown in FIG. 9, the status of one sensor can be reported in conjunction with the status of other sensors in the array. The signals from the array of sensors can be processed and analyzed in reference to each other, where appropriate. Software to report the status of biochemical interactions may include graphing tools for immediate viewing, wireless reporting of results to a remote site and other such schemes.

While the above detailed description has shown, described, and pointed out novel features of the invention as applied to various embodiments, it will be understood that various omissions, substitutions, and changes in the form and details of the device or process illustrated may be made by those skilled in the art without departing from the spirit of the invention. As will be recognized, the present invention may be embodied within a form that does not provide all of the features and benefits set forth herein, as some features may be used or practiced separately from others. The scope of the invention is indicated by the appended claims rather than by the foregoing description. All changes which come within the meaning and range of equivalency of the claims are to be embraced within their scope.

What is claimed is:

1. An optical system for determining information about an assay, comprising:

a laser comprising a laser resonating cavity, the laser resonating cavity comprising a gain medium, the laser resonating cavity configured to incorporate at least a portion of a filter assembly having a first and second surface, an assay disposed on the first surface, such that the first surface and the assay are disposed exterior to the laser resonating cavity and the second surface is disposed within the laser resonating cavity, wherein the laser resonating cavity is configured such that a reaction of the assay changes optical reflectance of the filter assembly and results in a change to a resonant characteristic of the laser resonating cavity that affects at least one characteristic of light propagating in the laser resonating cavity;

means for providing light to the laser resonating cavity; and means for determining information about a reaction in the assay by analyzing one or more characteristics of light propagating in the laser resonating cavity.

2. The system of claim 1, wherein the laser resonating cavity comprises means for holding at least a portion of the filter assembly in the laser cavity.

3. The system of claim 1, wherein the holding means comprises a vacuum.

4. The system of claim 1, wherein the light providing means comprises a light source in optical communication with the gain medium of the laser resonating cavity to provide light into the laser resonating cavity, wherein light propagating through the laser resonating cavity illuminates the second surface of the filter assembly held in the laser resonating cavity.

5. The system of claim 1, wherein the determining means comprises an analysis system in optical communication with the laser resonating cavity, and wherein the analysis system is configured to detect at least one characteristic of light propagating in the resonating cavity and to determine information relating to the assay based on the at least one characteristic.

6. The optical system of claim 1, wherein the optical reflectance change comprises a change of the refractive index of the filter assembly.

7. A method of determining information about an assay, comprising:
positioning a filter assembly to form a part of a laser resonating cavity, the laser resonating cavity comprising a gain medium, the filter assembly comprising
a first surface having an assay disposed thereon, and
a second surface comprising at least one thin film layer, the first surface and the assay being positioned exterior to the laser resonating cavity and the second surface being positioned to form an interior surface of the laser resonating cavity,
wherein the filter assembly is configured such that a reaction of the assay changes optical reflectance of the filter assembly and results in a change to a resonant characteristic of the laser resonating cavity that affects characteristics of light propagating in the laser resonating cavity;
propagating light in the laser resonating cavity such that light is reflected by the second surface within the laser resonating cavity; and
analyzing at least one characteristic of the light propagating in the laser resonating cavity to determine information about a reaction in the assay.

8. The method of claim 7, wherein the analyzed characteristic of the light is wavelength, intensity, frequency or phase.

9. The method of claim 7, wherein the analyzed characteristic of the light is wavelength.

10. The method of claim 7, wherein the analyzed characteristic of the light is frequency.

11. The method of claim 7, wherein a reaction that occurred in the assay is manifested in the characteristic of the light that is analyzed.

12. The optical system of claim 7, wherein the optical reflectance change comprises a change of the refractive index of the filter assembly.

13. An optical system for determining information about an assay comprising:
an optical structure comprising a laser having a laser resonating cavity, the laser resonating cavity comprising a gain medium, the laser resonating cavity configured to receive a filter assembly to form a part of the laser resonating cavity, the received filter assembly being positioned such that a first surface of the filter assembly is exterior to the resonating cavity and a second surface of the filter assembly forms an interior surface of the laser resonating cavity to reflect light propagating in the laser resonating cavity; and
a filter assembly removably attachable to the laser resonating cavity, the filter assembly comprising a first surface having an assay disposed thereon, and a second surface comprising at least one thin-film layer, wherein the filter assembly is configured such that a reaction of the assay changes optical reflectance of the filter assembly and results in a change to a resonant characteristic of the laser resonating cavity that affects at least one characteristics of light propagating in the laser resonating cavity.

14. The system of claim 13, further comprising an analysis system in optical communication with the optical structure to receive a portion of light from the laser resonating cavity, the analysis system configured to detect at least one characteristic of the received light and determine information relating to the assay based on the at least one detected characteristic.

15. The system of claim 14, further comprising a light source optically coupled to the gain medium of the laser resonating cavity to provide light into the laser resonating cavity, wherein light propagating through the laser resonating cavity illuminates the second surface of the filter assembly when the filter assembly is attached to the optical structure.

16. The system of claim 14, wherein the analysis system is further configured to determines information about a reaction on the assay based on the at least one detected characteristic.

17. The system of claim 13, wherein the at least one characteristic comprises wavelength.

18. The system of claim 13, wherein the at least one characteristic comprises frequency.

19. The system of claim 13, wherein the at least one characteristic comprises intensity.

20. The system of claim 13, wherein the at least one characteristic comprises phase.

21. The system of claim 13, wherein the optical structure further comprises a lens assembly configured to collimate light received by the filter assembly.

22. The system of claim 21, wherein the lens assembly is further configured to collimate light reflected from the filter assembly.

23. The system of claim 13, wherein the filter assembly comprises a Fabrey-Perot etalon filter.

24. The system of claim 13, wherein the filter assembly comprises a thin film stack.

25. The system of claim 13, wherein the filter assembly comprises a plurality of layers of SiO and $SiO_2$.

26. The system of claim 25, wherein the filter assembly comprises alternating layers of SiO and $SiO_2$.

27. The system of claim 13, further comprising a fluidic system for providing a fluidic analyte and assay to the first surface as a fluid.

28. The system of claim 13, wherein the filter assembly further comprises a plurality of layers, and wherein the filter assembly is further configured such that a change that occurs in the assay results in changing the optical path length of one or more of the plurality of layers.

29. The optical system of claim 13, wherein the optical reflectance change comprises a change of the refractive index of the filter assembly.

* * * * *